United States Patent [19]
Leggewie et al.

[11] Patent Number: 6,025,544
[45] Date of Patent: Feb. 15, 2000

[54] PROCESSES FOR MODIFYING PLANT FLOWERING BEHAVIOR

[75] Inventors: Georg Leggewie, Schmallenberg; Jorg Riesmeier, Berlin; Wolf-Bernd Frommer, Friedbergstr. 45, 14057 Berlin, all of Germany

[73] Assignees: Hoechst Schering AgrEvo GmbH; Wolf-Bernd Frommer, Berlin, Germany

[21] Appl. No.: 08/836,337

[22] PCT Filed: Oct. 30, 1995

[86] PCT No.: PCT/EP95/04257

§ 371 Date: Jul. 24, 1997

§ 102(e) Date: Jul. 24, 1997

[87] PCT Pub. No.: WO96/13595

PCT Pub. Date: May 9, 1996

[30] Foreign Application Priority Data

Oct. 31, 1994 [FR] France ................................. 44 39 748

[51] Int. Cl.[7] .......................... C12N 15/29; C12N 15/31; C12N 15/82; A01H 5/00
[52] U.S. Cl. ......................... 800/290; 800/278; 800/284; 800/288; 800/298; 800/306; 800/312; 800/314; 800/320; 800/320.1; 800/320.2; 800/323; 435/468; 536/23.6; 536/23.7
[58] Field of Search ................................. 435/172.3, 468; 800/205, 278, 284, 288, 290, 298, 306, 312, 314, 320, 320.1, 320.2, 323; 536/23.6, 23.7, 23.74

[56] References Cited

U.S. PATENT DOCUMENTS 5,608,146  3/1997  Frommer et al. ....................... 800/205
5,750,362  5/1998  Frommer et al. .......................... 435/29

FOREIGN PATENT DOCUMENTS

WO 94/00574  6/1994  WIPO .

OTHER PUBLICATIONS

Riesmeier et al. EMBOJ 11(13): 4705–4713, 1992.

Ohgawara et al. Protoplasma 116: 145–148, 1983.

Bockmann et al. "Characterization of a chromosomally encoded, non–PTS metabolic pathway for sucrose utilization in *Escherichia coli* EC3132," *Mol. Gen. Genet.* (1992) 235: 22–32.

Ebner et al. "DNA sequence of the gene scrA encoding the sucrose transport protein EnzymeII$^{Scr}$ of the phosphotransferase system from enteric bacteria: homology of the EnzymeII$^{Scr}$ and EnzymeII$^{Bgl}$ proteins," *Molecular Microbiology* (1988) 2: 9–17.

Bernier et al., "Physiological Signals That Induce Flowering", *The Plant Cell*, pp. 1147–1155, vol. 5, 1993.

Riesmeier, et al., "Evidence for an essential role of the sucrose transporter in phloem loading and assimilate partitioning", *EMBO Journal*, pp. 1–7, vol. 13, 1994.

*Primary Examiner*—David T. Fox
*Attorney, Agent, or Firm*—Fish & Neave; James F. Haley, Jr.; Karen E. Brown

[57] ABSTRACT

Described are processes for producing plants whose flowering behavior is modified in comparison to wildtype plants, in particular for producing plants with early flower formation and flowering to an increased extent, and the plants resulting from that process. Further, the use of DNA molecules encoding sucrose carriers for modifying plant flowering behavior is described.

15 Claims, 6 Drawing Sheets

PROCESSES FOR MODIFYING PLANT FLOWERING BEHAVIOR

This application is a 371 of PCT/EP95/04257 filed Oct. 30, 1995, which U.S.C. §119 from German patent application Ser. No. P 4439748.8, filed Oct. 31, 1994.

The present invention relates to processes for producing plants whose flowering behavior is modified in comparison with wildtype plants, in particular for producing plants which flower early and to an increased extent. The invention also concerns the plants resulting from that process. Such plants are produced by increasing the sucrose carrier activity in the plants. Furthermore, the invention relates to the use of DNA molecules which encode sucrose carriers in order to modify plant flowering behavior.

FIELD OF THE INVENTION

The flower formation is a precondition for the sexual propagation of plants and is therefore essential for the propagation of plants which cannot be propagated vegetatively as well as for the formation of seeds and fruits. The point of time at which the merely vegetative growth of plants changes into flower formation is of vital importance for example in agriculture, horticulture and plant breeding. Also the number of flowers is often of economic importance, for example in the case of various useful plants (tomato, cucumber, zucchini, cotton etc.) with which an increased number of flowers may lead to an increased yield, or in the case of growing ornamental plants and cut flowers.

For many fields of application it is advantageous if the plants flower early. In the field of agriculture, for example, early flowering would mean for various useful plants that the time between seeding and harvest is shortened and that therefore two harvests per year would be possible and that the period of time between flowering and harvest is prolonged so that an increased yield may be achieved. Also in the field of plant breeding early flowering could contribute to a considerable shortening of the breeding processes and could increase the profitability. It is obvious that early flowering would be economically useful also for horticulture and the growing of ornamental plants.

The research work previously done on the mechanisms that determine the point of time of flower formation of plants does not lead to a clear conclusion which factors are involved and determining. For a number of plants it is known that environmental influences determine the transition of vegetative growth to flower formation, for example light-darkness rhythms, temperature and water supply. It is hardly known how these stimuli are taken up and converted into physiological signals which induce the flower formation in the apical meristem. Various theories have been discussed and a number of possible factors have been taken into consideration, for example flowering hormones (florigen/antiflorigen), carbohydrates, cytokinins, auxin, polyamines and calcium ions (Bernier et al., Plant Cell 5 (1993), 1147–1155).

The control of the point of time of flower formation by regulating exogenous impulses, for example light-darkness rhythm, temperature or water supply, can be put into practice only to a limited extent, for example in greenhouses. In order to achieve early flowering of plants that are grown outdoors, it is necessary to use plants that flower early independent of exogenous impulses. Possibilities to grow such plants are offered by mutagenesis processes, which, however, cannot be applied for all species, by breeding processes, which are, however, very time consuming and have to be carried out separately for every plant species or by genetic engineering. The precondition, however, that genetic engineering can be applied is that gene loci are identified that have a considerable influence on the point of time of flowering and that there are DNA sequences that encode the relevant products. This, however, has not been the case.

For the specie *Arabidopsis thaliana,* which has been used most widely for research on the point of time of flowering, a number of mutants have been described which flower early in comparison to wildtype plants (see references in Lee et al., Plant Cell 6 (1994), 75–83), these mutants, however, have not been characterized any further. Also the detection of the biochemical factors that lead to early flowering has not been successful.

Bell et al., Plant Mol. Biol. 23 (1993), 445–451 describe tobacco plants that were transformed with the cdc25-cDNA from *Schizosaccharomyces pombe* and that show as a result of the expression of this mitosis inducing protein, early flowering and a substantially increased number of flowers. These plants, however, have the disadvantage of severe changes in leaf morphology. In particular, the leaves of these plants are curled.

Therefore, this process does not seem to be suitable to grow useful plants whose flowering behavior is modified.

Therefore, the growing of intact plants which show an increased number of flowers per plant or which flower early still depends on the conventional breeding processes or mutagenesis processes.

SUMMARY OF THE INVENTION

Therefore, the technical problem of the present invention is to modify the plants such that their flowering behavior is modified, in particular, such that they flower early and/or to an increased extent.

This problem is solved by providing the embodiments described in the claims.

Thus, the subject matter of the invention is the use of DNA molecules which encode proteins having the biological activity of a sucrose carrier in order to modify the flowering behavior of plants.

DETAILED DESCRIPTION OF THE INVENTION

In the published PCT application WO 94/00574 DNA sequences are described that encode sucrose carriers from spinach and potato. In this application the possibility is mentioned to introduce these sequences into plants along with DNA sequences for the regulation of the transcription with the aim of overexpressing such sucrose carriers. However, the use of DNA sequences that encode sucrose carriers for the modification of the flowering behavior of plants was not described.

It is assumed that the sucrose carrier plays an important role for the transport of sucrose—the most important transport form of the photoassimilates formed by photosynthesis—out of the photosynthetically active tissues into the phloem. It has been controversial to what extent the sucrose carrier also plays a role for the transport of sucrose out of the phloem into photosynthetically not active tissues that depend on the import of photoassimilates ("sink"-organs) (Riesmeier et al., Plant Cell 5 (1993), 1591–1598; Riesmeier et al., EMBO J. 13 (1994), 1–7).

A function of sucrose carriers for the regulation of the flowering behavior has not yet been taken into consideration. Sucrose has been discussed several times as a possible signal for the flowering induction in the apical meristem (Bernier et al., Plant Cell 5 (1993), 1147–1155; Lejeune et al., Planta 190 (1993), 71–74; Lejeune et al., Plant Physiol. Biochem. 29 (1991), 153–157), however, the influence of a sucrose carrier on the flowering behavior as a result of an increased activity of this carrier has not been known and, for several reasons, was also not to be expected.

It was surprisingly found that in transgenic plants in which the activity of the sucrose carrier in the tissues was increased in comparison to non-transformed plants a change in the flowering behavior could be observed. In the context of this application an increased activity of the sucrose carrier means that the sucrose activity in the transgenic plants is, in comparison to non-transformed plants, increased altogether, in particular by at least 30%, preferably by at least 50%, particularly preferred by at least 100%, and especially by at least 200%. Sucrose carriers are understood to be proteins that are capable of transporting sucrose across biological membranes. The activity of such carriers can be determined according to the method described in Riesmeier et al. (EMBO J. 11 (1992), 4705–4713). In the context of this application modified flowering behavior is understood such that in transformed plants in comparison with non-transformed plants a) the plants flower early, early meaning that the transformed plants in comparison to wildtype plants form flowers or flower at least some days earlier, preferably one to several weeks, in particular one to two weeks earlier, and/or b) flower to an increased extent, which means that the transformed plants in comparison to wildtype plants form in average more flowers per plant, usually at least 5% more flowers, in particular 10–100% and preferably 10–40% more flowers.

An increased sucrose carrier activity in comparison to wildtype plants can be achieved by the introduction of DNA molecules into plants that encode sucrose carriers. That way proteins with sucrose carrier activity are additionally synthesized in the transgenic cells. As a result, transformed tissues in which the introduced DNA molecule is expressed have, in comparison to non-transformed cells, an increased sucrose carrier activity.

In order to achieve an increase of the sucrose carrier activity in the tissues of plants, preferably the coding region of a DNA sequence that encodes a sucrose carrier is linked to DNA sequences that are necessary for the transcription in plant cells, and is introduced into plant cells. The regulatory sequences that are necessary for the transcription are promoters and, optionally, enhancer elements that are responsible for transcription initiation. Furthermore, termination signals that lead to the termination of the transcription as well as to the addition of a poly-A tail to the resulting transcript can be added, if necessary. These sequences are linked such that the coding region of a sucrose carrier gene is linked to the 3' end of the promoter in sense orientation so that an mRNA is synthesized which can be translated into a protein having the activity of a sucrose carrier, and that the 3' end of the coding region is followed by the termination signal.

Furthermore, the coding region can be linked to sequences that increase the translation in plant cells, as described in the examples.

The DNA molecules coding a sucrose carrier can be derived from any organism containing such sequences, in particular from any prokaryotic or eukaryotic organism. In a preferred embodiment, the DNA molecules are derived from plants, fungi or bacteria. In the case of plants higher plants are preferred, in particular monocotyledonous or dicotyledonous plants. DNA molecules encoding sucrose carriers are already known from various organisms and are mentioned below. These are preferably used in this invention.

The invention also relates to a process for modifying the flowering behavior of plants, the flowering behavior being effected by increasing the activity of the sucrose carrier in plants.

Transgenic plants that show a modified flowering behavior in comparison to non-transformed plants, in particular early flowering and/or flowering to an increased extent, are produced by means of a process comprising the following steps:

a) construction of an expression cassette comprising the following DNA sequences:
   i) a promoter functional in plant cells that guarantees the transcription of the resulting DNA sequence,
   ii) at least one DNA sequence that encodes a sucrose carrier and that is linked to the 3' end of the promoter in sense orientation, and
   iii) if necessary, a termination signal for the termination of the transcription and the addition of a poly-A-tail to the resulting transcript that is linked to the 3' end of the coding region, b) transformation of plant cells with the expression cassette constructed in step a) and stable integration of the expression cassette into the plant genome, and c) regeneration of complete, intact plants from the transformed plant cells.

The promoter mentioned in i) can be, in principle, any promoter functional in plants. Suitable is, for example, the 35S promoter of the cauliflower-mosaic virus (Odell et al., Nature 313 (1985), 810–812), which guarantees a constitutive expression in all tissues of a plant and the promoter construct as described in WO/9401571. However, also promoters can be used that lead only at a point of time determined by external influences (see, for example, WO/9307279) or in a certain tissue of the plant to an expression of the sequences linked to them (see, for example, Hadash et al., Plant Cell 4(1992), 149–159, Stockhaus et al., EMBO J. 8 (1989), 2245–2251).

The DNA molecules comprising a coding region for a sucrose carrier can be both of native, that is homologous origin, and of foreign, that is heterologous origin, with respect to the plant species to be transformed. Both DNA molecules from prokaryotic organisms and those from eukaryotic organisms, in particular plants, can be used. Prokaryotic sequences are, for example, known from *E.coli* (Bockmann et al., Mol. Gen. Genet. 235 (1992), 22–32; EMBL gene bank: accession number X63740).

A preferred embodiment is the use of DNA molecules coding plant sucrose carriers. Known are, for example, RNA and DNA sequences from Arabidopsis thaliana (suc 1- and suc 2-genes; EMBL gene bank: accession numbers X75365 and X75382, respectively, as well as H36128, H36415, R64756, T76707 and T42333), *Solanum tuberosum* (Riesmeier et al., Plant Cell 5 (1993), 1591–1598; EMBL gene bank: accession number X69165 and WO 94/00547), *Plantago major* (EMBL gene bank: accession numbers X75764 and X84379), *L. esculentum* (EMBL gene bank: accession numb er X82275), *Nicotiana tabacum* (EMBL gene bank: accession numbers X82276 and X82277), *R. communis* (EMBL gene bank: accession number Z31561), *B. vulgaris* (EMBL gene bank: accession number X83850) and rice (EMBL gene bank: accession numbers D40522 and D40515), which encode sucrose carriers. A special embodiment of the present invention provides for the use of a DNA molecule from *Spinacia oleracea*, which encodes a sucrose carrier (see also Riesmeier et al., EMBO J. 11 (1992), 4705–4713 and WO 94/00547).

A further preferred embodiment of the process according to the invention is the use of DNA molecules encoding sucrose carriers having $K_m$ values which are as low as possible. Such carrier activity is, for example, known from *Candida albicans* (Williamson et al., Biochem. J. 291 (1993), 765–771).

The molecules encoding sucrose carriers can be both cDNA molecules and genomic sequences. The DNA molecules can be isolated from the respective organisms by means of conventional methods known to the person skilled in the art, for example hybridizing or polymerase chain reaction, or they can be produced synthetically.

The termination signals for the transcription in plant cells mentioned in section iii) are described and interchangeable. For example, the termination sequence of the nopalin synthase gene from *Agrobacterium tumefaciens* (see, e.g., Gielen et al., EMBO J. 8 (1989), 23–29) can be used. The described expression cassette can also contain DNA sequences that increase the translation of the coding region in plant cells.

The method according to the invention can in principle be applied to any flower forming plant species, preferably to the plants mentioned below.

The subject matter of the invention further comprises transgenic plants which, due to the increased activity of the sucrose carrier, show a modified flowering behavior in comparison to wildtype plants, in particular early flower formation and flowering and/or flowering to an increased extent.

Such transgenic plants are preferably obtained by the above described process. That means that in these plants the increase of the sucrose carrier activity is preferably based on the introduction of DNA molecules into the plants encoding a sucrose carrier and on their expression. The DNA molecules are preferably derived from plants, fungi or bacteria.

The plants according to the invention are preferably monocotyledonous or dicotyledonous useful plants, for example cereals (such as barley, oats, rye, wheat etc.), corn, rice, vegetables (such as tomato, melon, zucchini etc.), cotton, rapeseed, soy bean, fruits (such as plum, apple, pear etc.), ornamental flowers or cut flowers.

For the preparation of the introduction of foreign genes into higher plants a great number of cloning vectors is available containing a replication signal for *E.coli* and a marker gene for the selection of transformed bacteria cells. Examples of such vectors are pBR322, pUC series, M13mp series, pACYC184 etc. The desired sequence can be introduced into the vector at a suitable restriction cleavage site. The obtained plasmid is used for the transformation of *E.coli* cells. Transformed *E.coli* cells are cultivated in a suitable medium, then harvested and lysed. The plasmid is recovered. As analyzing methods for the characterization of the recovered plasmid DNA usually restriction analyses, gel electrophoreses and further biochemical molecular biological methods are used. After every manipulation the plasmid DNA can be cleaved and linked to other DNA sequences. Every plasmid DNA sequence can be cloned in the same or in other plasmids.

For the transformation of plant cells by means of the expression cassette described in the process plasmids are preferably used.

For the introduction of DNA into a plant host cell a number of methods can be used. The methods comprise the transformation of plant cells with T-DNA using *Agrobacterium tumefaciens* or *Agrobacterium rhizogenes* as transformation means, fusion of protoplasts, injection, electroporation of DNA, introduction of DNA by means of the biolistic methods, as well as further possibilities.

The plasmids used do not have to fulfill special requirements for the injection and electroporation of DNA in plant cells. Simple plasmids such as pUC derivatives can be used. If, however, whole plants are to be regenerated from such transformed cells, the presence of a selectable marker gene is necessary.

Depending on the method for the introduction of desired genes into the plant cells, further DNA sequences may be necessary. If, for example, the Ti- or Ri-plasmid is used for the transformation of the plant cell, at least the right border, often, however, also the right and left border of the Ti- and Ri-plasmid T-DNA has to be linked as flanking region to the genes to be introduced.

If Agrobacteria are used for the transformation, the DNA to be introduced has to be cloned into special plasmids, that is either into an intermediate vector or into a binary vector. The intermediate vectors can, due to sequences that are homologous to sequences in the T-DNA, be integrated into the Ti- or Ri-plasmid of the agrobacteria by means of homologous recombination. The Ti- or Ri-plasmid furthermore contains the vir region necessary for the transfer of the T-DNA. Intermediate vectors cannot replicate in Agrobacteria. By means of a helper plasmid the intermedium vector can be transferred to *Agrobacterium tumefaciens* (conjugation). Binary vectors can replicate both in *E.coli* and in Agrobacteria. They contain a selection marker gene and a linker or polylinker, which are flanked by the right and the left T-DNA border region. They can be transformed directly into the agrobacteria (Holsters et al., Mol. Gen. Genet. 163 (1978), 181–187). The agrobacterium, which serves as host cell, should contain a plasmid containing a vir region. The vir region is necessary for the transfer of the T-DNA into the plant cell. Additional T-DNA may be present. The Agrobacterium transformed such is used for the transformation of plant cells.

Intensive research work was done on the use of T-DNA for the transformation of plant cells and is sufficiently described in EP 120516; Hoekema, In: The Binary Plant Vector System Offsetdrukkerij Kanters B.V., Alblasserdam, Chapter V; Fraley et al., Crit. Rev. Plant. Sci., 4 (1985), 146 and An et al., EMBO J. 4 (1985), 277–287.

For the transfer of the DNA into the plant cell it is suitable to co-cultivate plant explants with *Agrobacterium tumefaciens* or *Agrobacterium rhizogenes*. From the infected plant material (for example leaf explants, segments of stems, roots but also protoplasts or suspension cultivated plant cells) whole plants can be regenerated in a suitable medium which may contain antibiotics or biozides for the selection of transformed cells. The plants obtained that way can then be examined for the presence of the introduced DNA.

Once the introduced DNA has been integrated into the genome of the plant cell, it usually is stable there and is also contained in the progenies of the originally transformed cell. It usually contains a selection marker which makes the transformed plant cells resistant to a biozide or an antibiotic such a kanamycin, G418, bleomycin, hygromycin or phosphinotricin and others. Therefore, the individually chosen marker should allow the selection of transformed cells from cells lacking the introduced DNA.

The transformed cells grow within the plant in the usual way (see also McCormick et al., Plant Cell Reports 5 (1986), 81–84). The resulting plants can be cultured normally and be cross-bred with plants possessing the same transformed genetic information or other genetic information. The hybrid individuals resulting therefrom possess the corresponding phenotype features.

Two or more generations should be cultivated to make sure that the phenotype feature is maintained stably and is transmitted. Seeds should be harvested to make sure that the corresponding phenotype or other properties are maintained.

A=Fragment A: CaMV 35S promoter, nt 6909-7437 (Franck et al., Cell 21 (1980), 285–294). In the 5' region of the promoter two 35S enhancer elements (330 bp HincII/EcoRV fragment) were inserted into the Nco I cleavage site B=Fragment B: Nco I/Asp 718 fragment (TMV-U1) having a length of 73 bp with the translation enhancer from the tobacco mosaic virus C=Fragment C: DNA fragment having a length of about 1600 bp, comprising the nucleotides 70 to 1644 of the cDNA encoding the sucrose carrier from spinach (Riesmeier et al., EMBO J. 11 (1992), 4705–4713)

D=Fragment D: DNA fragment having a length of 33 bp, encoding the amino acid sequence EQKLISEEDLN-COOH E=Fragment E: termination sequence of the octopin synthase gene; nt 11748-11939 of the T-DNA of the Ti plasmid pTiACH5 (Gielen et al., EMBO J. 3 (1984), 835–846)

The fragments A, B, C, D and E are contained in the vector pUC18. The plasmid has a size of about 5700 bp.

Figure 2:
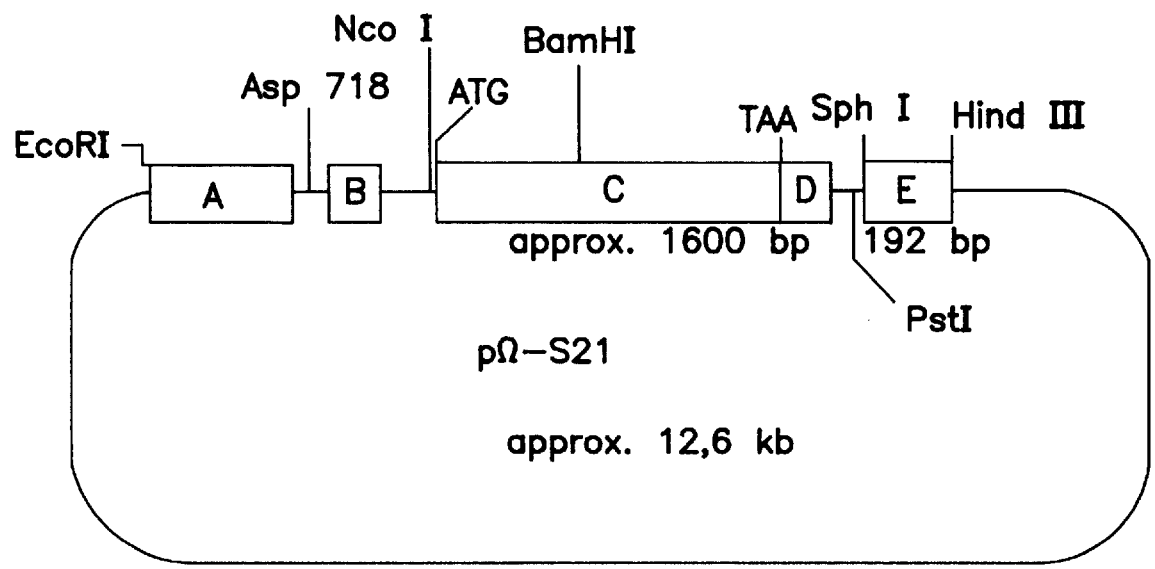

FIG. 2 shows the plasmid pΩ-S21.

A=Fragment A: CaMV 35S promoter, nt 6909-7437 (Franck et al., Cell 21 (1980) 285–294). In the 5' region of the promoter two 35S enhancer elements (330 bp HincII/EcoRV fragment) were inserted into the Nco I cleavage site.

B=Fragment B: Nco I/Asp 718 fragment (TMV-U1) having a length of 73 bp with the translation enhancer from the tobacco mosaic virus C=Fragment C: DNA fragment with a length of about 1600 bp comprising the nucleotides 70 to 1644 of the cDNA that encodes the sucrose carrier from spinach (Riesmeier et al., EMBO J. 11 (1992), 4705–4713)

D=Fragment D: DNA fragment with a length of 33 bp encoding the amino acid sequence EQKLISEEDLN-COOH E=Fragment E: termination sequence of the octopin synthase gene; nt 11748-11939 of the T-DNA of the Ti plasmid pTiACH5 (Gielen et al., EMBO J. 3 (1984), 835–846)

The plasmid has a size of about 12.6 kb.

Figure 3:
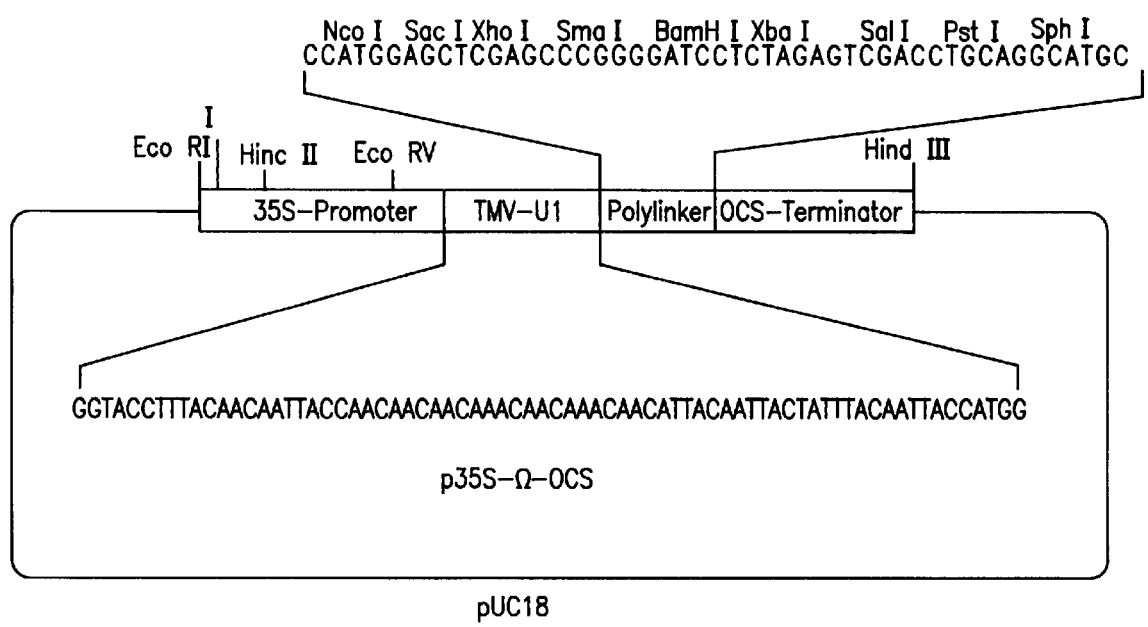

FIG. 3 shows the plasmid p35 S-Ω-OCS.

FIG. 4 and b show transformed tobacco plants in comparison to non-transformed tobacco plants.

a: Three plants of tobacco line 12, which had been transformed with the plasmid pΩ-S21 (foreground) are shown in comparison to two non-transformed tobacco plants (background). The plants are about 128 days old and were kept in the phytotron.

b: Three plants of tobacco line 32, which had been transformed with the plasmid pΩ-S21, (background) are shown in comparison to two non-transformed tobacco plants (foreground). The plants are about 128 days old and were kept in the phytotron.

Figure 5:
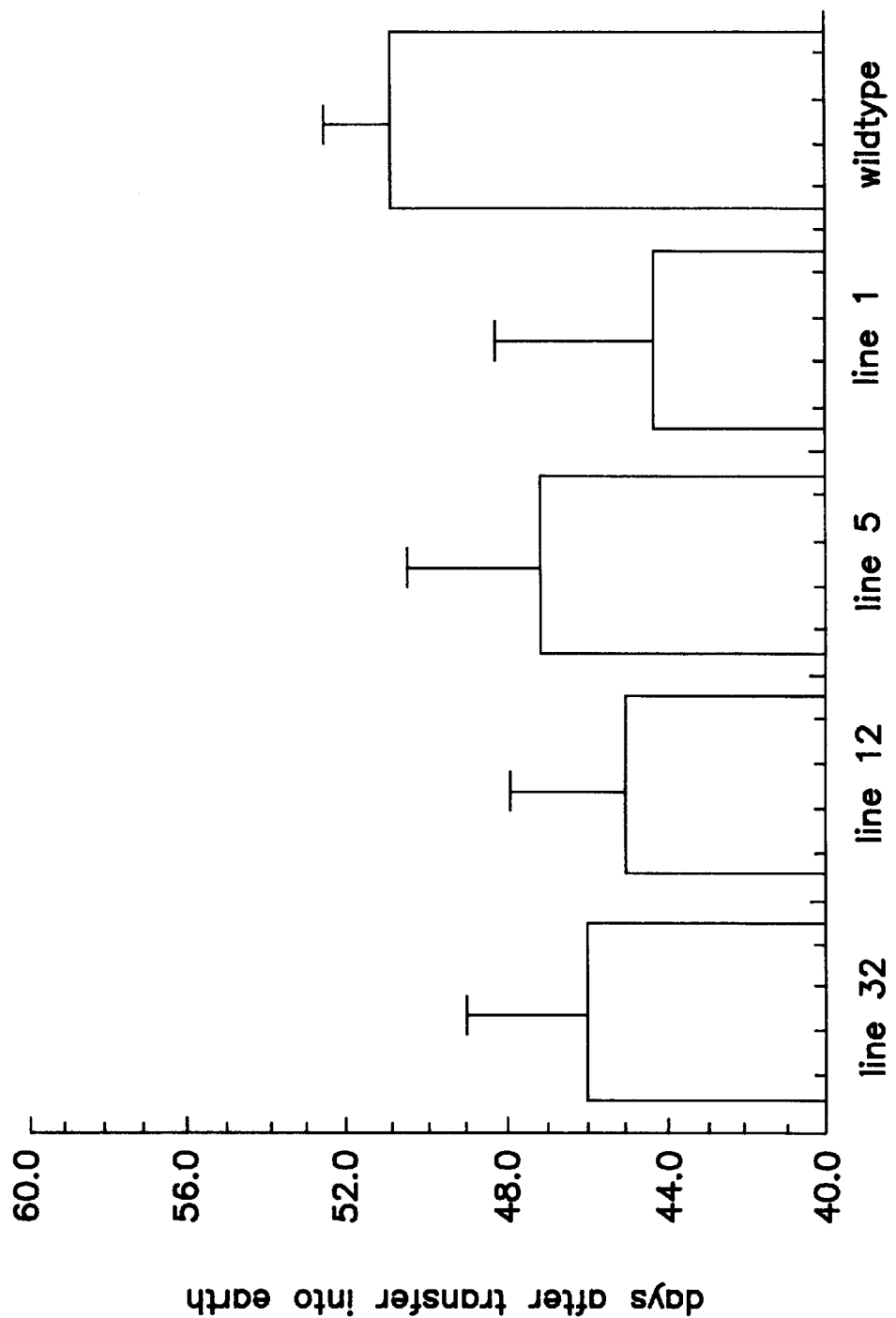

FIG. 5 shows as a bar chart the average number of days between the transfer of the plants from the tissue culture into earth until the opening of the first flower. 12 plants per genotype were grown with the following light conditions in a phytotron.

| | |
|---|---|
| 7–9 a.m. | 300 $\mu$mol quanta m$^2$ sec$^{-1}$ |
| 9–11 a.m. | 600 $\mu$mol quanta m$^2$ sec$^{-1}$ |
| 11 a.m.–1 p.m. | 900 $\mu$mol quanta m$^2$ sec$^{-1}$ |
| 1–5 p.m. | 1200 $\mu$mol quanta m$^2$ sec$^{-1}$ |
| 5–7 p.m. | 900 $\mu$mol quanta m$^2$ sec$^{-1}$ |
| 7–9 p.m. | 600 $\mu$mol quanta m$^2$ sec$^{-1}$ |
| 9–11 p.m. | 300 $\mu$mol quanta m$^2$ sec$^{-1}$ |

Figure 6:
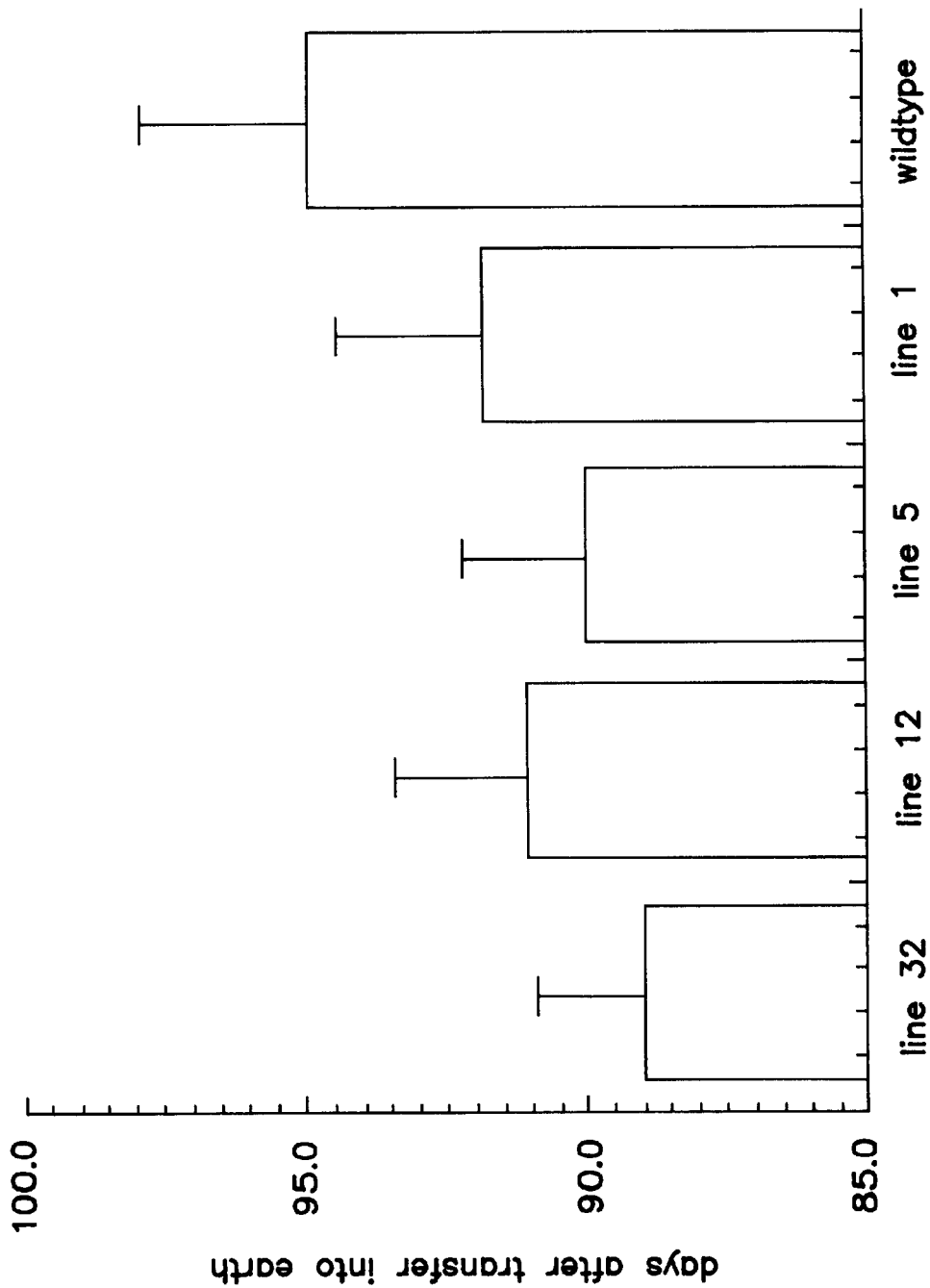

FIG. 6 shows as a bar chart the average number of the days between the transfer of the plants from the tissue culture into earth until the opening of the first flower. 12 plants per genotype were grown with the following light conditions in a phytotron. The lines 32, 12, 5 and 1 are four independent transgenic lines which had been transformed with the plasmid pΩ-S21.

| | |
|---|---|
| 7 a.m.–11 p.m. | 400–500 $\mu$mol quanta m$^{-2}$ sec$^{-1}$ |

Figure 7:
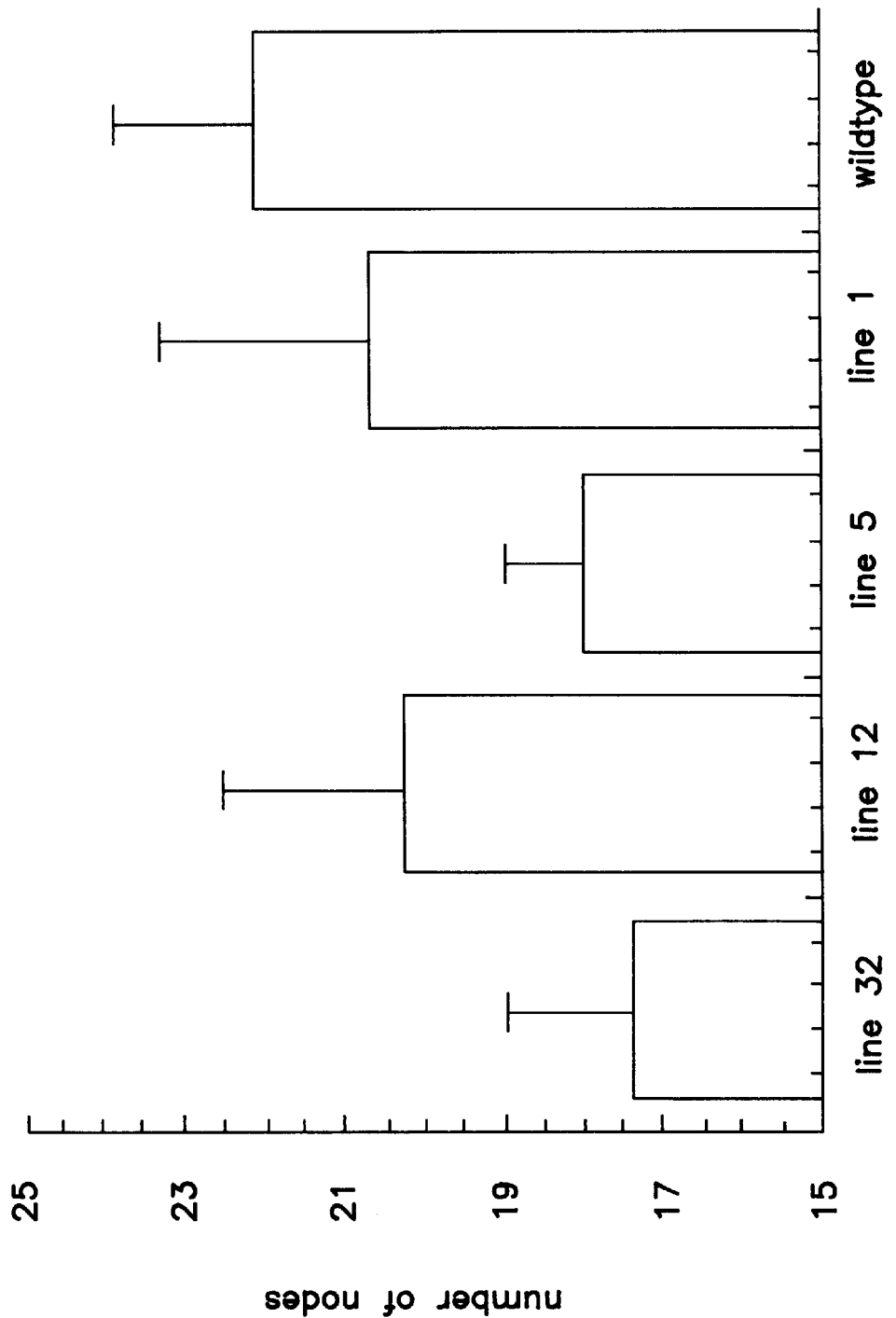

FIG. 7 shows as a bar chart the average number of leaf bases until the formation of the flower. Test conditions see FIG. 6.

EXPERIMENTAL METHODS

Media and solutions used in the examples

| | |
|---|---|
| 20 × SSC | 175.3 g NaCl |
| | 88.2 g natrium citrate |
| | ad 1000 ml with ddH$_2$O |
| | pH 7.0 with 10 NNaOH |
| 10 × MEN | 200 mM MOPS |
| | 50 mM natrium acetate |
| | 10 mM EDTA |
| | pH 7.0 |
| NSEB buffer | 0.25 M natrium phosphate buffer pH 7.2 |
| | 7% SDS |
| | 1 mM EDTA |
| | 1% BSA (weight/volume) |
| 4 × Laemlli buffer | 200 mM tris pH 6.8 |
| | 8% SDS |
| | 0.4% bromophenol blue |
| | 40% glycerol |

Methods used in the examples:

1. Cloning process

For the cloning in *E.coli* the vector pUC18 was used.

For the plant transformation the gene constructions were cloned in the binary vector pBinAR (Höfgen and Willmitzer, Plant Sci. 66 (1990), 221–230).

2. Bacteria strains

For the pUC vectors and for the pBinAR constructs the *E.coli* strain DH5α (Bethesda Research Laboratories, Gaithersburgh, USA) were used.

The transformation of the plasmids in the tobacco plants was effected with the help of the *Agrobacterium tumefaciens* strain C58C1 pGV2260 (Debleare et al., Nucl. Acids Res. 13 (1985), 4777–4788).

3. Transformation of *Agrobacterium tumefaciens*

The transfer of the DNA was effected by direct transformation using the method of Höfgen & Willmitzer (Nucleic Acids Res. 16 (1988), 9877). The plasmid DNA of transformed Agrobacteria was isolated using the method of Birnboim & Doly (Nucleic Acids Res. 7 (1979), 1513–1523) and, upon suitable restriction cleavage, analyzed by gel electrophoresis.

4. Transformation of tobacco

An overnight culture of the respective *Agrobacterium tumefaciens* clone was centrifuged (6500 rpm; 3 min.) and the bacteria were resuspended in a YEB medium. Tobacco leaves of a tobacco sterile culture (*Nicotiana tabacum* cv. Samsun NN) were cut into small pieces with a seize of about 1 cm² each and bathed in a bacteria suspension. The leaf pieces were then put on MS medium (0.7% agar) and incubated in darkness for 2 days. Then the leaf pieces were put on MS medium (0.7% agar) for shoot induction with 1.6% glucose, 1 mg/l 6-benzylaminopurin, 0.2 mg/l naphthyle acetic acid, 500 mg/l claforan and 50 mg/l kanamycin. The medium was exchanged every 7 to 10 days. Upon shoot induction the leaf pieces were transferred into glass containers containing the same medium. Forming shoots were cut off and put on MS medium+2% sucrose+250 mg/l claforan and whole plants were regenerated from them.

5. Radioactive labeling of DNA fragments

The radioactive labeling of DNA fragments was effected by means of a DNA random primer labeling kit of th e company Boehringer (Germany) according to the manufacturer's instructions.

6. Northern blot analysis

RNA was isolated from leaf tissue of plants according to standard protocols. 50 μg of the RNA were separated (1.5 agarose, 1×MEN buffer, 16.6% formaldehyde). The gel was shortly washed in water after the gel run. The RNA was transferred to a nylon membrane of the type Hybond N (Amersham UK) with 20×SSC by means of blotting. The membrane was then baked for two hours under vacuum at a temperature of 80° C. The membrane was prehybridized in NSEB buffer for 2 hours at a temperature of 68° C. and subsequently hybridized overnight in the presence of the radioactively labeled probe at 68° C. in NSEB buffer.

7. The isolation of proteins from leaf tissue and Western blot analysis

For the isolation of proteins from leaf tissue two perfectly circular leaf explants with a diameter of about 5 mm were punched from tobacco leaves and triturated in 100 μl 4×Laemmli buffer, 5% β-mercaptoethanol in an Eppendorf vial. The resulting suspension was shortly centrifuged. 10 μl of the supernatant was put directly on a "MighTy Small" SDS polyacryl amid gel of the company Höfer (separation gel 10% polyacrylamid: collection gel 3.5% polyacrylamid) and separated by gel electrophoresis. The proteins were then transferred on a nitrocellulose membrane by means of the semidry electroblot method. The identification of the sucrose carrier from spinach in the extracts of transgenic tobacco plants was effected using a "blotting detection kit—for rabbit antibodies" (Amersham UK) according to the producer's instructions. As a primary antibody the monoclonal antibody from mouse 9E10 (Kolodziej and Young, In: Methods in Enzymology 194 (1991), 508–519) is used, which is directed against the myc epitope shown in FIG. 1 as fragment D.

8. Plant maintenance

In the greenhouse:

| | |
|---|---|
| light period | 14 h at 1300 lux and 25° C. |
| dark period | 10 h at 20° C. |
| humidity | 60% |

In the phytotron:

| | |
|---|---|
| light period | 15 h at 800 mEinstein/m²/sec at 25° C. |
| dark period | 9h at 22° C. |
| humidity | 80% |

The examples illustrate the invention.

EXAMPLE 1

Construction of the Plasmid pΩ-S21 and Introduction of the Plasmid into the Genome of Tobacco Plants For the construction of a plasmid which is suitable for the transformation of plant cells and which leads to the overexpression of a sucrose carrier in plant cells first the coding region of a cDNA encoding a sucrose carrier from spinach was isolated. For this purpose the clone pS21 (described in Riesmeier et al., EMBO J. 11 (1992), 4705–4713) was used. Using the oligonucleotides (1)
5'-GAGACTGCCAAGCCATGGCAGGAAGAAATATA TAAAAAATGGTG-3'(SEQ ID NO: 1) and (2)
5'-GAGACTGCAGTCAGTTGAGGTCTTCTTCGGAG ATTAGTTTTTGTTC ATGACCACCCATGGACCCACCMTTTTAGC-3'(SEQ ID NO: 2)

a DNA fragment having a length of about 1600 bp and comprising the nucleotides 70 to 1644 of the sequence of the clone pS21 described in Riesmeier et al. (EMBO J. 11 (1992), 4705–4713) was amplified by means of PCR technology. By means of oligonucleotide (1) a Pst I and an Noc I cleavage site was introduced at the 5' end of the coding region. By means of oligonucleotide (2) a sequence (EQKLISEEDLN-COOH (SEQ ID NO: 3)) with a length of 11 amino acids was added to the coding region at the C terminus and furthermore a Pst I cleavage site was introduced. This sequence stems from the c-Myc gene and represents the site of recognition for the monoclonal antibody from mouse 9E10 (Kolodziej and Young, In: Methods in Enzymology 194 (1991), 508–519; commercially available at Dianova, Hamburg).

The resulting PCR product was cut with the restriction endocuclease Pst I and ligated with a pUC18 vector cut with Pst I. The resulting plasmid was named p-S21-Myc8. From this a fragment of a size of about 1600 bp was isolated by Nco I/Pst I partial digestion which contains the PCR product and into which the vector p35SDE-Ω-OCS cut with Nco I and Pst I was ligated.

The vector p35SDE-Ω-OCS was produced as follows:

From the promoter region of the cauliflower mosaic virus an EcoR I/Asp718 fragment with a length of 530 bp (nucleotides 6909-7439 (Franck et al. Cell 21 (1980), 285–294)) was isolated and ligated into a pUC18 vector cut with EcoRI and Asp718. The resulting plasmid was called p35S. Then a fragment with a length of about 330 bp was isolated from the EcoR I/Asp718 promoter fragment by restriction digestion with the endonucleases Hinc II and EcoR V. This fragment was then cloned into the filled in Nco I cleavage site of the 35S promoter in the plasmid p35S. A construct resulted in which two Hinc II/EcoR V-I fragments behind each other in reverse orientation were inserted in the Nco I cleavage site with the following arrangement:

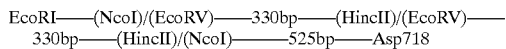

The resulting plasmid was called p35SDE. The 35S promoter contained in this fragment comprising two additional Hinc II/EcoR V fragments was called 35SDE.

A further pUC plasmid was constructed which is structured as shown in FIG. 3. The following DNA fragments were inserted between the EcoR I and the Hind III cleavage sites of the polylinker of a pUC18 vector:

1. EcoR I/Asp718 fragment of the 35S promoter (nucleotides 6909-7439 (Franck et al., Cell 21 (1980), 285–294))
2. Asp718/Nco I fragment (TMV-U1) from the Q translation enhancer of the tobacco mosaic virus with the following sequence:
5'-GGTACCTTTACAACAATTACCAACAACAACAAAC AACAAACAACAT TACAATTACTATTTACAATTACCATGG-3'(SEQ ID NO: 4)
3. a polylinker with the following restriction cleavage sites Nco I/Sac I/Xho I/Sma I/BamH I/Xba I/Sal I/Pst I/Sph I
4. a termination sequence from the octopine synthase gene (nt 11748-11939 of the T-DNA of the Ti plasmid pTiACH5 (Gielen et al., EMBO J. 3 (1984), 835–846) This plasmid was called p35S-Ω-OCS.

The plasmid p35S-Ω-OCS was cleaved with EcoR I/Asp718, thereby removing the 35S promoter. The 35S promoter was replaced with the promoter 35SDE, which was isolated from the plasmid p35SDE by EcoR I and Asp718. The resulting plasmid was called p35SDE-Ω-OCS.

Figure 1:
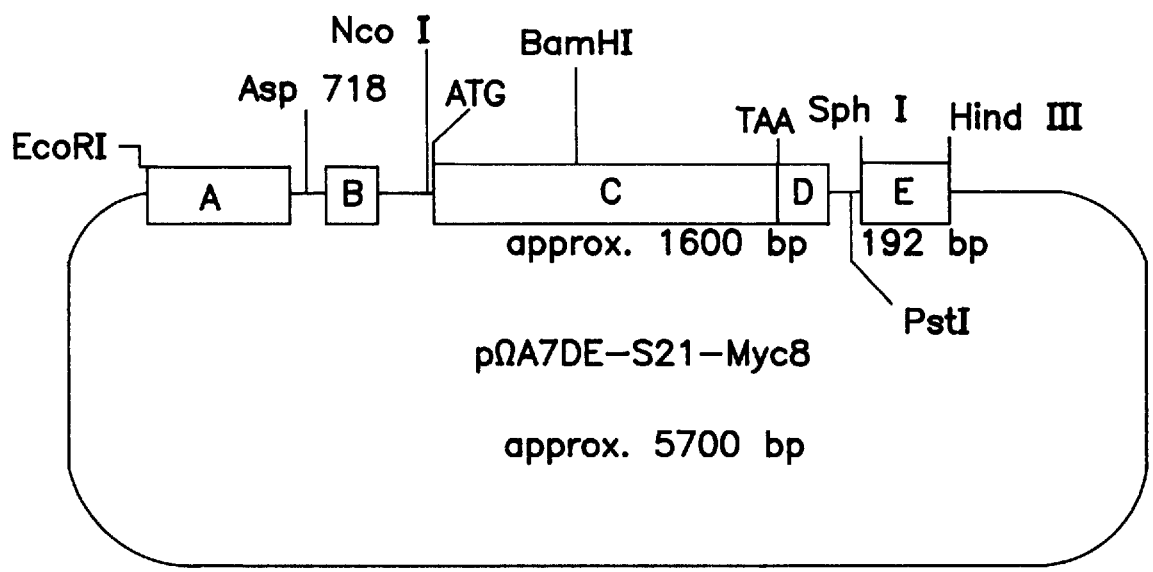
FIG. 1 shows the plasmid pΩ2A7DE-S21-Myc8.

This plasmid was cut with Nco I and Pst I in the polylinker. Into the cleavage sites the fragment with a length of about 1600 bp, which was isolated from the plasmid p-S21-Myc8 by partial digestion with Nco I and Pst I and contains the above-described pCR product, was ligated. The plasmid pΩA7DE-S21-Myc8 resulted therefrom. This plasmid is shown in FIG. 1.

From the plasmid pΩA7DE-S21-Myc8 the complete expression cassette comprising the promoter 35SDE, the translation enhancer, the coding region encoding the sucrose carrier from spinach with the sequence encoding the c-Myc epitope and with the termination sequence was isolated by means of digestion with EcoR I and Hind III.

This sequence was ligated into the vector TCSAS cut with EcoR I and Hind III (deposited at the culture collection institute Deutsche Sammlung von Mikroorganismen in Braunschweig, Germany, on Aug. 10, 1994 under Accession No. DSM 9359), from which the expression cassette contained between these two restriction cleavage sites had previously been removed by the digestion of EcoR I/Hind III.

The resulting plasmid was called pΩ-S21 and is shown in FIG. 2.

Example 2

Transformation of Tobacco Plants with the Plasmid pΩ-S21

The plasmid pΩ-S21 was used for the transformation of tobacco plants by means of the gene transfer induced by Agrobacteria.

As a result of the transformation the transcript encoding the sucrose carrier from spinach could be detected in various amounts in transgenic tobacco plants. The detection was effected by means of a Northern Blot analysis. For this analysis RNA was isolated from the leaf tissue of transgenic and non-transformed plants. 50 μg of this RNA were separated on a agarose gel, transferred to a nylon membrane and hybridized with the radioactively labeled cDNA encoding the sucrose carrier from spinach. Such Northern blot analysis showed that two transformants (nos. 12 and 32) out of three transformants (nos. 5, 12 and 32) show high expression of the sucrose carrier from spinach, that one transformant (no. 5) in comparison showed relatively low expression of the sucrose carrier from spinach and that in non-transformed potato plants no transcripts were detected encoding the sucrose carrier from spinach.

In order to show that the transcript encoding a sucrose carrier from spinach leads in transgenic tobacco plants to the synthesis of a sucrose carrier, a Western Blot analysis was performed. For this purpose proteins were isolated from the leave tissue of transgenic plants, separated on an SDS gel and transferred to a nitrocellulose membrane. The detection of the spinach sucrose carrier was effected in transgenic tobacco plants by means of monoclonal antibodies which recognize the epitope of the c-Myc gene, which is encoded from the 3'end of the coding region in the plasmid pΩ-S21.

In such Western blot analyses a protein of about 48 kD could be detected specifically in protein extracts of transgenic tobacco plants. This corresponds to the expected molecular weight of the sucrose carrier from spinach.

Due to the expression of the sucrose carrier from spinach the tobacco plants transformed with the plasmid pΩ-S21 showed in comparison to non-transformed tobacco plants a modified flowering behavior. Particularly with transformants 12 and 32, which showed high expression of the spinach sucrose carrier, early flowering as well as flowering to a slightly increased extent could be observed.

Transformed tobacco plants showed in comparison to non-transformed plants significantly fewer leaf bases prior to the induction of the apical meristem for the formation of flowers. It is shown in Table I how many leaf bases about 128 days-old, transformed and non-transformed tobacco plants maintained in the phytotron showed in average before the differentiation of the apical meristem to inflorescence.

TABLE I

| transformed tobacco line no. | average number of leaf bases |
| --- | --- |
| 5 | 17.8 |
| 12 | 18 |
| 32 | 17.3 |
| non-transformed plants | 20.7 |

Figure 4A:
Figure 4B:

Due to the early induction of the meristem for the formation of inflorescences buds and flowers form early in comparison to wildtype plants. This is also illustrated by FIGS. 4a and b, which show transformed tobacco plants kept in the phytotron of line 12 (FIG. 4a) and line 32 (FIG. 4b), respectively, in comparison to non-transformed tobacco plants. Under the same culturing conditions with non-transformed tobacco plants the flower formation and flowering took place significantly later, on average about 14 days later than the plants kept in the phytotron.

Apart from early flowering the transformed plants displayed an increased number of flowers in comparison to wildtype plants. This is shown in Table II.

TABLE II

| transformed tobacco line no. | average number of leaf bases |
| --- | --- |
| 5 | 112 |
| 12 | 170 |
| 32 | 133 |
| non-transformed plants | 103 |

The plants examined were about 128 days old and had been kept in the phytotron.

The results described above confirmed in a repeated experiment during which plants of the transformed lines 32, 12, 5 and 1 were examined. The results are shown in FIGS. 5, 6 and 7.

We claim:

1. A transgenic plant with a modified flowering behavior in comparison to the wildtype, said modified flowering behavior comprising early flowering and flower formation or flowering to an increased extent, wherein the plant exhibits an increased sucrose carrier activity in comparison to the wildtype as a result of the integration and expression of a DNA molecule, which molecule encodes in the sense orientation a sucrose carrier from bacteria.

2. A process for modifying plant flowering behavior, comprising the steps of:

(a) transforming a plant cell with a DNA molecule which encodes in the sense orientation a sucrose carrier;

(b) producing a transgenic plant comprising the transformed plant cell; and (c) growing the transgenic plant under conditions in which the DNA molecule is expressed and the transgenic plant exhibits modified flowering behavior compared to a wildtype plants;

wherein expression of the DNA molecule increases the sucrose carrier activity in the transgenic plant and wherein said modified flowering behavior comprises early flowering and flower formation.

3. The process according to claim 2, wherein the DNA molecule encodes in the sense orientation a plant sucrose carrier.

4. The process according to claim 2, wherein said modified flowering behavior further comprises flowering to an increased extent.

5. The process according to claim 2, wherein said transgenic plant is selected from the group consisting of a cereal plant, corn, rice, a vegetable plant, cotton, rapeseed, soy bean, a fruit plant, and an ornamental flower plant.

6. The process according to claim 2, wherein the DNA molecule is part of an expression cassette comprising a promoter functional in the transformed plant cells, the promoter being operably linked to the DNA molecule.

7. The process according to claim 6, wherein the expression cassette further comprises a termination signal downstream of the DNA molecule.

8. The transgenic plant according to claim 1, wherein said modified flowering behavior comprises early flowering and flower formation.

9. The transgenic plant according to claim 1, wherein said modified flowering behavior comprises flowering to an increased extent.

10. The transgenic plant according to claim 1, wherein said modified flowering behavior comprises early flowering and flower formation and flowering to an increased extent.

11. The transgenic plant according to claim 1, wherein said transgenic plant is selected from the group consisting of a cereal plant, corn, rice, a vegetable plant, cotton, rapeseed, soy bean, a fruit plant, and an ornamental flower plant.

12. A process for modifying plant flowering behavior, comprising the steps of:

(a) transforming a plant cell with a DNA molecule which encodes in the sense orientation a sucrose carrier from bacteria;

(b) producing a transgenic plant comprising the transformed plant cell; and (c) growing the transgenic plant under conditions in which the DNA molecule is expressed and the transgenic plant exhibits modified flowering behavior compared to a wildtype plant;

wherein expression of the DNA molecule increases the sucrose carrier activity in the transgenic plant and wherein said modified flowering behavior comprises early flowering and flower formation or flowering to an increased extent.

13. The process according to claim 12, wherein said modified flowering behavior comprises early flowering and flower formation and flowering to an increased extent.

14. The process according to claim 12, wherein said transgenic plant is selected from the group consisting of a cereal plant, corn, rice, a vegetable plant, cotton, rapeseed, soy bean, a fruit plant, and an ornamental flower plant.

15. The process according to claim 12, wherein the DNA molecule is part of an expression cassette comprising a promoter functional in the transformed plant cells, the promoter being operably linked to the DNA molecule.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(iii) HYPOTHETICAL: YES (iv) ANTI-SENSE: NO (xi) SEQUENCE DESCRIPTION: SEQ ID NO:1:

GAGACTGCAG CCATGGCAGG AAGAAATATA TAAAAAATGG TG      42

(2) INFORMATION FOR SEQ ID NO:2:

(i) SEQUENCE CHARACTERISTICS:
      (A) LENGTH: 76 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(iii) HYPOTHETICAL: YES (iv) ANTI-SENSE: NO (xi) SEQUENCE DESCRIPTION: SEQ ID NO:2:

GAGACTGCAG TCAGTTGAGG TCTTCTTCGG AGATTAGTTT TTGTTCATGA CCACCCATGG      60

ACCCACCAAT TTTAGC      76

(2) INFORMATION FOR SEQ ID NO:3:

(i) SEQUENCE CHARACTERISTICS:
      (A) LENGTH: 11 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:3:

Glu Gln Lys Leu Ile Ser Glu Glu Asp Leu Asn

-continued

```
1               5              10
```

(2) INFORMATION FOR SEQ ID NO:4:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO:4:

GGTACCTTTA CAACAATTAC CAACAACAAC AAACAACAAA CAACATTACA ATTACTATTT      60

ACAATTACCA TGG      73